United States Patent
Moeller (10) Patent No.: US 11,660,397 B2
(45) Date of Patent: May 30, 2023

(54) AUTO INJECTOR WITH IMPROVED FUNCTIONALITY

(71) Applicant: Shally Engineering Plastics Ltd., Gujarat (IN)

(72) Inventor: Claus Schmidt Moeller, Fredensborg (DK)

(73) Assignee: SHAILY ENGINEERING PLASTICS LTD., Gujarat (IN)

( * ) Notice: Subject to any disclaimer, the term of this patent is extended or adjusted under 35 U.S.C. 154(b) by 394 days.

(21) Appl. No.: 17/043,991

(22) PCT Filed: Mar. 30, 2019

(86) PCT No.: PCT/DK2019/000120
§ 371 (c)(1),
(2) Date: Sep. 30, 2020

(87) PCT Pub. No.: WO2019/192662
PCT Pub. Date: Oct. 10, 2019

(65) Prior Publication Data
US 2021/0030962 A1   Feb. 4, 2021

(30) Foreign Application Priority Data

Mar. 30, 2019   (DK) .......................... PA 2018 00144

(51) Int. Cl.
*A61M 5/315* (2006.01)
*A61M 5/20* (2006.01)
(Continued)

(52) U.S. Cl.
CPC ...... *A61M 5/2033* (2013.01); *A61M 5/31585* (2013.01); *A61M 5/326* (2013.01);
(Continued)

(58) Field of Classification Search
CPC ............ A61M 5/2033; A61M 5/31585; A61M 5/326; A61M 5/31528; A61M 5/3202;
(Continued)

(56) References Cited

U.S. PATENT DOCUMENTS

2005/0273055 A1* 12/2005 Harrison ............... A61M 5/326
604/198
2013/0060232 A1*  3/2013 Adlon ................. A61M 5/2066
604/82

(Continued)

FOREIGN PATENT DOCUMENTS

CN      102264417 B      1/2014
EP       0516473 A1      12/1992
(Continued)

OTHER PUBLICATIONS

International Search Report (Form PCT/ISA/210) for International Patent Application No. PCT/DK2019/000120, issued from the European Patent Office, dated Jun. 18, 2019, 3 pages.
(Continued)

*Primary Examiner* — Nathan R Price
*Assistant Examiner* — Sarah Dympna Grasmeder
(74) *Attorney, Agent, or Firm* — Kilyk & Bowersox, P.L.L.C.

(57) ABSTRACT

The invention relates to an auto injector, by which a fixed dose of a medicament can be injected as self-treatment, and by which needle exposure to an accessible position, injection of the medicament and retraction of the needle to an inaccessible position is automatically performed as a continuous sequence, after the auto injector is triggered. The invention provides solutions to improve the functionality of the retraction of the needle and the general experience of the use.

11 Claims, 8 Drawing Sheets

(51) Int. Cl.
    *A61M 5/32*    (2006.01)
    *A61M 5/50*    (2006.01)
    *A61M 5/31*    (2006.01)

(52) U.S. Cl.
    CPC ... *A61M 5/5086* (2013.01); *A61M 2005/3143* (2013.01); *A61M 2205/584* (2013.01)

(58) Field of Classification Search
    CPC .... A61M 2005/3143; A61M 2005/206; A61M 2005/2703
    See application file for complete search history.

(56) References Cited

U.S. PATENT DOCUMENTS

| | | | |
|---|---|---|---|
| 2013/0310757 A1* | 11/2013 | Brereton | A61M 5/3257 604/197 |
| 2016/0317753 A1* | 11/2016 | Jugl | A61M 5/20 |

FOREIGN PATENT DOCUMENTS

| | | |
|---|---|---|
| EP | 2468329 A1 | 6/2012 |
| JP | 2012-506745 A | 3/2012 |
| WO | 9535126 A1 | 12/1995 |
| WO | 2005115509 A1 | 12/2005 |
| WO | 2005115511 A1 | 12/2005 |
| WO | 2005115513 A1 | 12/2005 |
| WO | 2005115516 A1 | 12/2005 |
| WO | 2007066152 A2 | 6/2007 |
| WO | 2008005315 A2 | 1/2008 |
| WO | 2008113199 A1 | 9/2008 |
| WO | 2010049239 A1 | 5/2010 |
| WO | 2011101377 A1 | 8/2011 |
| WO | 2012045831 A1 | 4/2012 |
| WO | 2017007850 A1 | 1/2017 |

OTHER PUBLICATIONS

Written Opinion of the International Searching Authority (Form PCT/ISA/237) for International Patent Application No. PCT/DK2019/000120, issued from the European Patent Office, dated Jun. 18, 2019, 6 pages.

* cited by examiner

AUTO INJECTOR WITH IMPROVED FUNCTIONALITY

FIELD OF THE INVENTION

The invention relates to an auto injector, by which a fixed dose of a medicament can be injected as self-treatment, and by which needle exposure to an accessible position, injection of the medicament and retraction of the needle to an inaccessible position is automatically performed as a continuous sequence, after the auto injector is triggered.

BACKGROUND FOR THE INVENTION

Through the last two decades the use of auto injectors has increased significantly every year as they have the benefit that they allow patients to take their medication without involving a doctor or a nurse. Automated needle insertion, injection and needle retraction is state of the art for this type of auto injectors and new auto injectors enters the market regularly. As users of this type of auto injectors often are first time users, it is essential that the auto injectors are easy to use, smooth in operation and reliable, but unfortunately this is not the case for many auto injectors on the market.

For a first time user the act of injection a medicament into his own body can be very stressful, and it is therefore very important that the auto injector is easy to understand and to handle, as the stressful situation can lead to an incorrect use of the auto injector with a risk of mistreatment. It is also important that the injection is carried out smoothly, with the correct injection speed and without accompaniment of high and scarring noises, to prevent that the injection is painful or unnecessarily scarring. And last the auto injectors should work every time to prevent that this type of auto injectors are being associated with uncertainty and misbelieve.

The most common problems with auto injectors is non-intuitive handling and complicated instructions, expelling of medicament beginning before the needle is inserted to the correct depth, too fast injection of the medicament, and after retraction of the needle it is loud noises when the auto injector shift from one functional sequence to another, and malfunction of the auto injector, especially related to the retraction of the needle.

DESCRIPTION OF THE RELATED ART

The patent field for auto injectors is very crowded, but the documents WO9535126, EP0516473, WO2005115509, WO2005115511, WO2005115513, WO2005115516, WO2007066152, WO2008005315, WO2011101377, EP2468329 and EP2129416 give a good description of the prior art in the field. Some of these will be further described hereafter.

In WO2005115516 an auto injector comprising a housing adapted to receive a syringe with a hollow needle is described. The housing includes means for biasing the syringe from an extended position in which the needle extends from the housing to a retracted position in which the needle is contained within the housing. The auto injector further comprises a compressible spring, a drive acted upon by the spring and in turn acting on the syringe to discharge its contents through the needle, a decoupling mechanism, activated when the drive has been advanced to a nominal decoupling position, to allow a first component of the auto injector to move relative to a second, a release mechanism, activated when the said first component has reached a nominal release position relative to the second, to release the syringe from the action of the spring, whereupon the biasing means restores the syringe to its retracted position, and a highly viscous fluid is damping the movement of the said first component relative to the second, so that the release of the syringe is delayed after the activation of the decoupling mechanism to allow the remaining contents of the syringe to be discharged before the syringe is released for retraction.

In WO2008005315 another auto injector for providing a subcutaneous injection of a substance into a user is described, comprising a housing, a syringe with a barrel portion holding the substance and with a needle attached movably disposed in the housing, and a plunger for sealing the barrel portion and selectively applying pressure to the substance to force the substance through the needle, a syringe actuation component for first moving the syringe towards the first end of the housing such that the needle is exposed and for subsequently applying pressure to the plunger, and a compressible spring for biasing the syringe actuation component towards the proximal end of the housing, the spring disposed between a flange on the syringe actuation component and the distal end of the housing.

Both of the described auto injectors make use of compression springs for insertion and retraction of the needle and for injection, which in turn requires a number of couplings and locking/unlocking features to shift between the different operational sequences, and which therefore increases the risk of a malfunction. Secondly both auto injectors push on the plunger to move the syringe forward, which increases the risk of starting the injection before the needle is fully inserted. Furthermore, compression springs tends to give a very unsmooth operation.

The auto injector described in WO2011101377 makes use of a torsion spring to insert and retract the needle and for injection. The auto injector comprises an elongate outer housing arranged to contain a syringe with a hollow needle and a plunger, the outer housing having a distal end and a proximal end with an orifice intended to be applied against an injection site. The syringe is slidably arranged with respect to the outer housing, and the auto injector further comprises a torsion spring capable of, upon activation: 1) pushing the needle into an advanced position through the orifice and, 2) operating the syringe to supply the dose of medicament, and finally 3) retracting the syringe with the needle into the covered position after delivering the medicament and after the syringe has been unlocked from the advanced position. Activating means are arranged to lock the spring in a pressurized state prior to manual operation and capable of, upon manual operation, releasing the torsion spring for injection, the torsion spring being grounded at one end in the outer housing and at the other end in a first gear member rotatable about a longitudinal axis. The first gear member is arranged to, upon rotation, translatively move a second gear member toward the proximal end, where the second gear member is prevented from rotating and coupled to the plunger in order to push it towards the proximal end, and the first gear member is engaged with the activating means prior to manual operation in a manner to prevent rotation and disengaged from the activating means upon manual operation.

Due to the torsion spring this auto injector will provide a smoother injection compared to the other described auto injectors, but the auto injector still comprises locking/unlocking features with a consequently increased risk of malfunction between the different functional sequences.

It is the objective of the invention to provide an auto injector, which does not comprise any active mode shifting elements for actively enabling and/or disabling different sequences of the auto injector, and which clearly distinguish in time between needle insertion injecting and needle retraction and with no overlap of the sequences.

BRIEF DESCRIPTION OF THE INVENTION

The invention relates to an auto injector defining a main axis and comprising:
a housing,
a syringe assembly comprising a container with a hollow needle and a plunger and the medicament to be injected,
a first spring means,
a driver,
screw,
a trigger adapted to initiate the functional sequences of the auto injector after activation wherein the functional sequences includes moving the syringe assembly in the housing to expose the needle to an accessible position, expelling of the medicament out through the needle, and moving the syringe assembly in the housing to retract the needle to an inaccessible position, and wherein the screw during injection is adapted to move the plunger in the container to expel the medicament by means of the first spring means and via the driver, and wherein the first spring means is a torsion spring acting on the driver and moving the driver up in the housing away from the needle end of the housing at least during expelling of the medicament and retraction of the needle.

By letting the driver move up in the auto injector new options for retraction of the needle is provided so that a specific mode shifting mechanism is not required.

In another embodiment an auto injector according to the invention has the spring means in one end fixed to the syringe assembly and in the other end to the driver. In this way contraction or compression of the torsion spring is prevented during the movement of the syringe assembly to retract the needle to an inaccessible position.

In yet another embodiment the screw and the driver are rotational connected so that they rotate together but are allowed to telescope, and so that the movement of the plunger is the result of a rotational movement of the screw relative to the syringe assembly in a first thread engagement, or the screw and the driver are engaged in a thread engagement and the movement of the plunger is the result of a rotational movement of the driver relative to the screw in a first thread engagement.

By rotating the screw down in a thread engagement with another element the axial movement of the screw is being more smooth and precise.

In yet another embodiment the driver is engaging the housing in a second thread engagement at least during expelling of the medicament, and the second thread engagement disengages immediately after the expelling to allow the driver and the syringe assembly by means of a second springs means to move into the housing to a position where the needle is inaccessible. By having the retraction of the needle being initiated by a thread disengagement it is ensured that the components involved in the retraction operation will not block.

In yet another embodiment the driver is engaging the housing in a second thread engagement at least during expelling of the medicament, and the second thread engagement disengages immediately after the expelling to allow the driver and the syringe assembly by means of contraction of the first springs means to move into the housing to a position where the needle is inaccessible. By letting the first spring means being fixed to the housing and the driver and at the same time letting the first spring means retract the needle, a second spring means for the retraction of the needle is unnecessary.

In yet another embodiment the syringe assembly and the driver are, during exposure of the needle, engaged in a third thread engagement and the movement of the syringe assembly is a result of relative rotational movement between the syringe assembly and the driver. By letting a rotational movement and a thread performing the movement of the syringe assembly the speed and speed variation can be controlled by the pitch of the thread and possible by designing the thread as a variable pitch thread.

In yet another embodiment the syringe assembly after initiation by the trigger is moved toward the needle end of the housing by means of a third spring means being a compressible spring. In this way a more rapid needle insertion can be provided if this should be desired.

In yet another embodiment the length and position of the thread on the screw is arranged such, that rotation of the screw in the first thread engagement does not move the plunger in the cartridge during exposure and retraction of the needle. In this way it is ensured, that there is a clear separation between the functional sequences of the auto injector, and that expelling of medicament does not occur during exposure and retraction of the needle.

In yet another embodiment the functional sequences of the auto injector start after an axial movement of the driver relative to the syringe assembly and initiated by the trigger. By simply pushing the syringe assembly out of the rotational connection with the driver, a very simple trigger system can be provided.

In yet another embodiment the trigger is a sleeve movable arranged on the outside of the housing, and the trigger must be rotated an angle relative to the housing to enable initiation of the functional sequences of the auto injector, where after axial movement of the trigger initiates the functional sequences. This takes away the need for an additional and separate enabling mechanism to ensure that the auto injector is fired by accident.

In yet another embodiment a damper is rotatable arranged inside the syringe assembly and is rotationally connecting to the screw in the end of or immediately after the expelling of medicament to slow down the speed of the screw by means of friction. This ensures in a very simple and reliable way that the plunger is fully relaxed, and the medicament fully expelled before the needle is retracted.

The objective of the invention can be obtained by an auto injector having a torsion spring as the driving spring for insertion and injection of the medicament. A cartridge with a hollow needle and containing the medicament is contained in a syringe assembly, which is rotational secured relative to a housing. The syringe assembly comprises a cartridge carrier having an orifice with a thread positioned over the opening of the cartridge, wherein a screw can be screwed down in a first thread engagement against a plunger in the cartridge to move the plunger down in the cartridge and press out the medicament through the needle. A driver is rotational but not axial connected with the screw, and the screw and the driver can telescope relative to each other. The driver is further more engaged with the housing in the end opposite the needle in a second thread engagement. The torsion spring is in one end secured to the syringe assembly and in the other end secured to the driver. The syringe assembly further comprises a connecting tube fixed to the cartridge carrier, and the connecting tube and the driver are engaged with each other in a key/groove connection before the auto injector is triggered, followed by a third and a fourth thread engagement after each other after the auto injector is triggered, where the pitches of the threads forming the second and fourth thread engagements are the same, and where the pitch of the threads in the third thread engagement is higher than of the threads in the second and fourth thread engagements. A trigger sleeve surrounding the housing is adapted to be capable of pushing the connecting tube out of the key/groove engagement with the driver, when the auto injector is pressed against an injection site and the trigger sleeve is moved relative to the housing.

After a user has triggered the auto injector by pressing it against the skin, and the key/groove connection between the connecting tube and the driver consequently is pushed out of engagement, the connecting tube enters into the third thread engagement with the driver, and the torsion spring rotates the driver, and due to the thread engagement move the connecting tube and thereby the syringe assembly forward to expose the needle and insert it in subcutaneous tissue. Hereafter the connecting tube and the driver enters into the fourth thread engagement, and as the driver moves up due to the second thread engagement with the housing, and as the threads of the second and the fourth thread engagements have the same pitch, the syringe assembly will not move. The screw, however, will be rotated down in the cartridge due to the first thread engagement with the cartridge carrier, and the medicament is injected. When the content of the cartridge is injected, the second thread engagement between the driver and the housing is rotated out of engagement, and a return spring pushes the syringe assembly back into the auto injector until the syringe assembly is stopped by the trigger sleeve and the needle is fully retracted.

To ensure that the full content is expelled before the needle is retracted, the screw rotationally connects to a damper, which slows down the rotational speed of the screw and the driver, before the driver disengages the thread of the housing. The damper is positioned inside the cartridge carrier and high viscosity grease or other frictional compounds or materials is applied between the damper and the cartridge carrier.

To enable the trigger sleeve to fire the auto injector the trigger sleeve must be rotated from a locking position to an enabled position relative to the auto injector. This is to ensure that the auto injector is not fired by accident during handling.

FIGURES

In the following the invention is described in further details with reference to the drawings, wherein.

DETAILED DESCRIPTION

In the following the term main axis defines the common axis of revolution for the mainly tube-shaped parts and for the entire auto injector. The terms "up" and "down" and "upper" and "lower" and "upward" and "downward" refer to the drawings and does not necessarily correspond to a situation of use.

Figure 1:
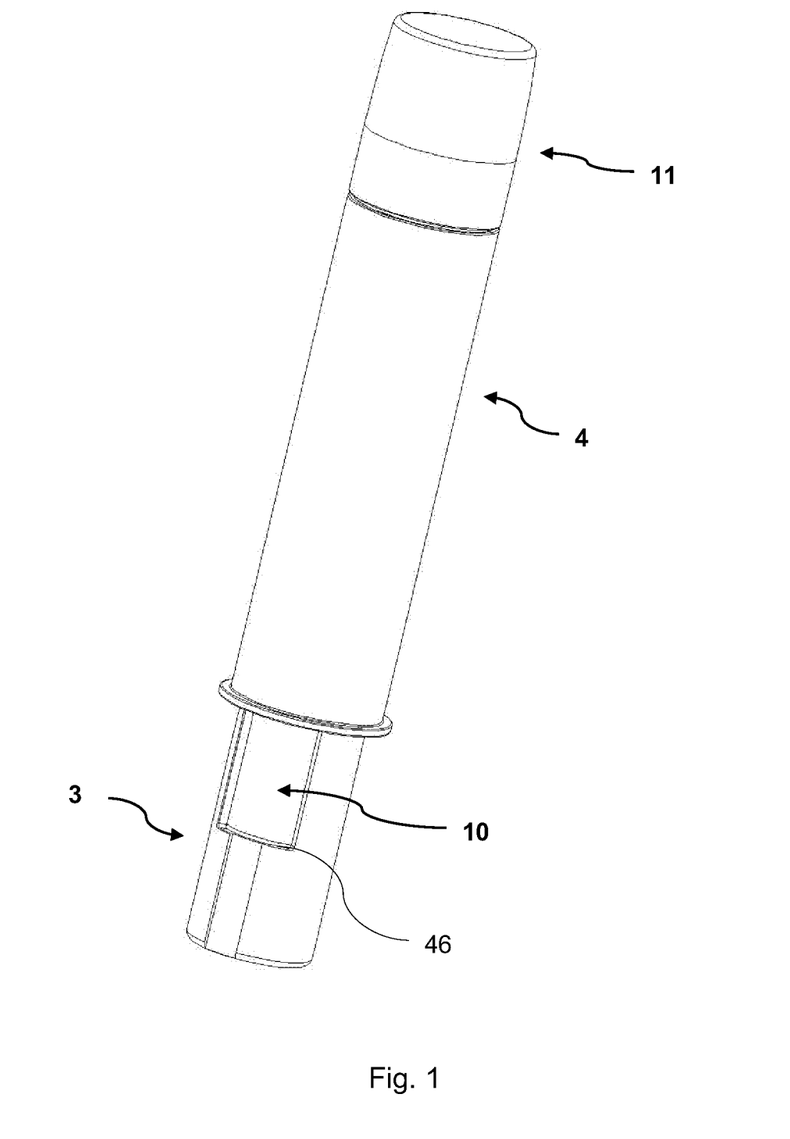
FIG. 1 shows a perspective view of an auto injector according to the invention.

In FIG. 1 a perspective view of an auto injector according to the invention is shown. At the upper part of the auto injector the upper housing 11 can be seen, and in the lower part the lower housing 3, protruding all the way up to the upper housing 11, can be seen. Also, the window 46 for viewing the content of the cartridge 10 is visible. A trigger sleeve 4, by which the functional sequences of the auto injector is initiated, is visible outside the housing 3, and the auto injector is operated by gripping around the trigger sleeve 4 and pressing the auto injector against the injection site. The auto injector is prepared for injection by rotating the trigger sleeve 4 an angle from a locking position to an enabled position, where after axial movement of the trigger sleeve 4 relative to the housing 3 is possible, which in turn will initiate the sequences of exposing the needle, injecting the medicament and retracting the needle. Alternatively, the auto injector is unlocked by removing a cap (not shown) covering the lower part of the housing and the cartridge 10, and the cap can be adapted to remove the needle shield (not shown) at the same time.

Figure 2:
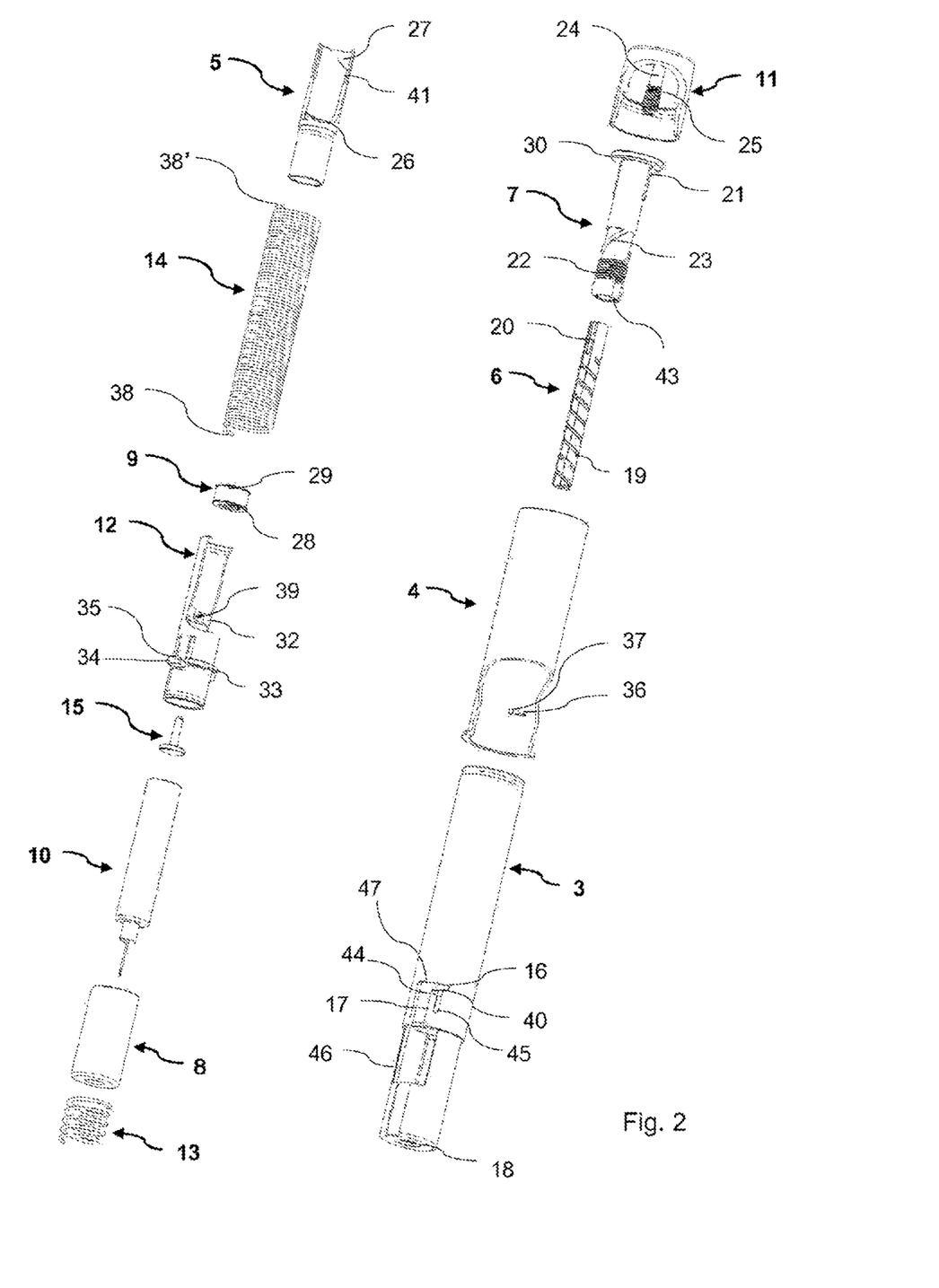
FIG. 2 shows an exploded view of an auto injector according to the invention.
Figures 3, 4:
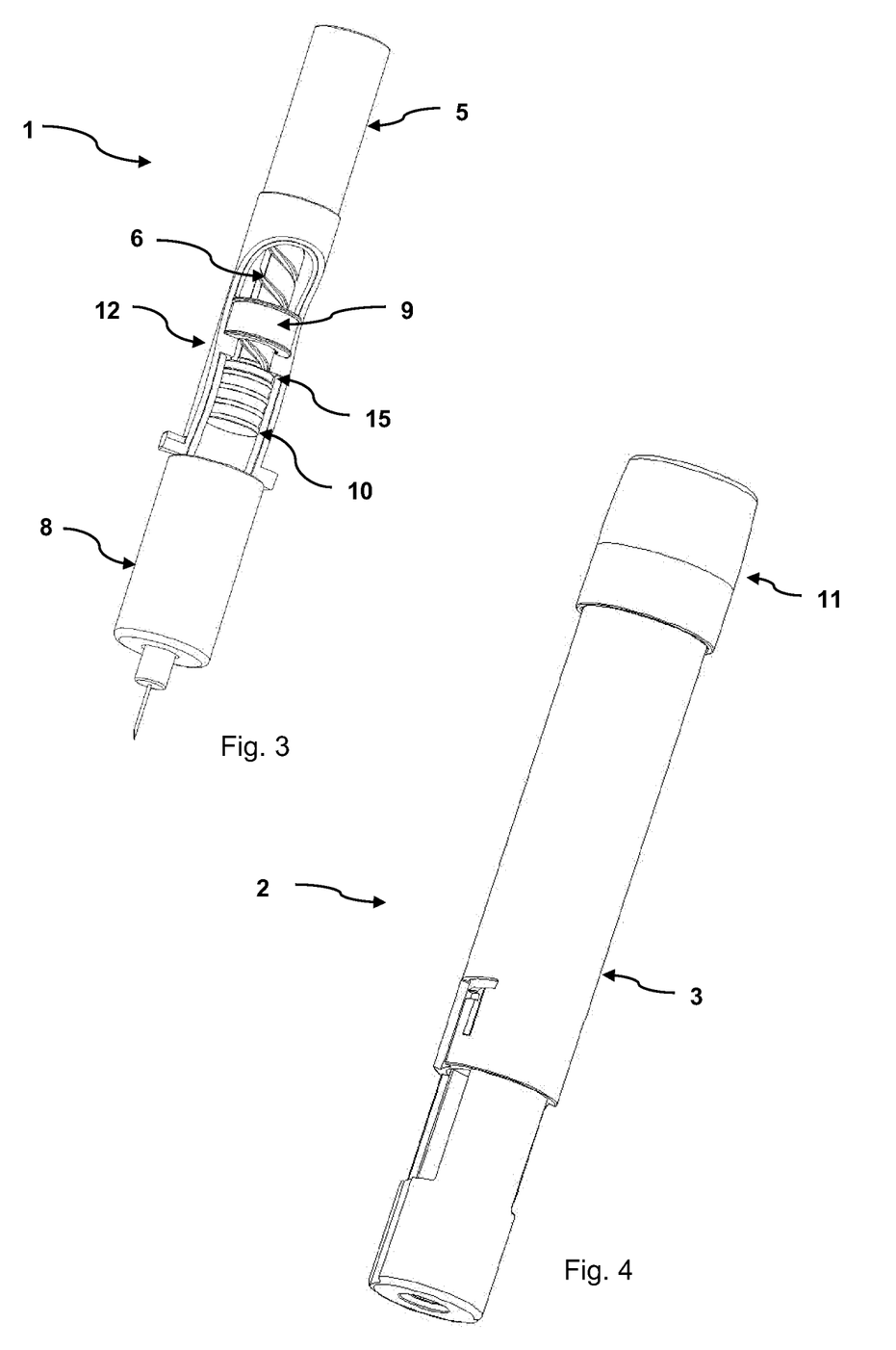
FIG. 3 shows a perspective and partly sectioned view of the syringe assembly according to the invention.
FIG. 4 shows a perspective view of the housing assembly according to the invention.

FIG. 2 shows an exploded view of an auto injector according to the invention with all parts of the auto injector visible. These will be referred to during the functional descriptions, especially when the sectional views do not clearly show the described feature. Some parts of the auto injector are fixed together to act as one part, e.g. the cartridge carrier 12, the cartridge aligner 8, the connecting tube 5 and the cartridge 10 with the needle, plunger and medicament, and these parts, together with the screw 6, the plunger foot 15 and the damper 9, forms the syringe assembly 1. This can be seen in FIG. 3. Also, the lower housing 3 and the upper housing 11 are fixed together and acts as one part, and the two parts together are in the following referred to as the housing 2 and can be seen in FIG. 4. It should be understood that these assemblies could in fact be divided differently or divided to form more or less parts depending on how the auto injector is supposed to be assembled, and that the cartridge 10 can be made of glass or plastic and be a separate part or integrated with other parts of the syringe assembly 1.

Figure 5:
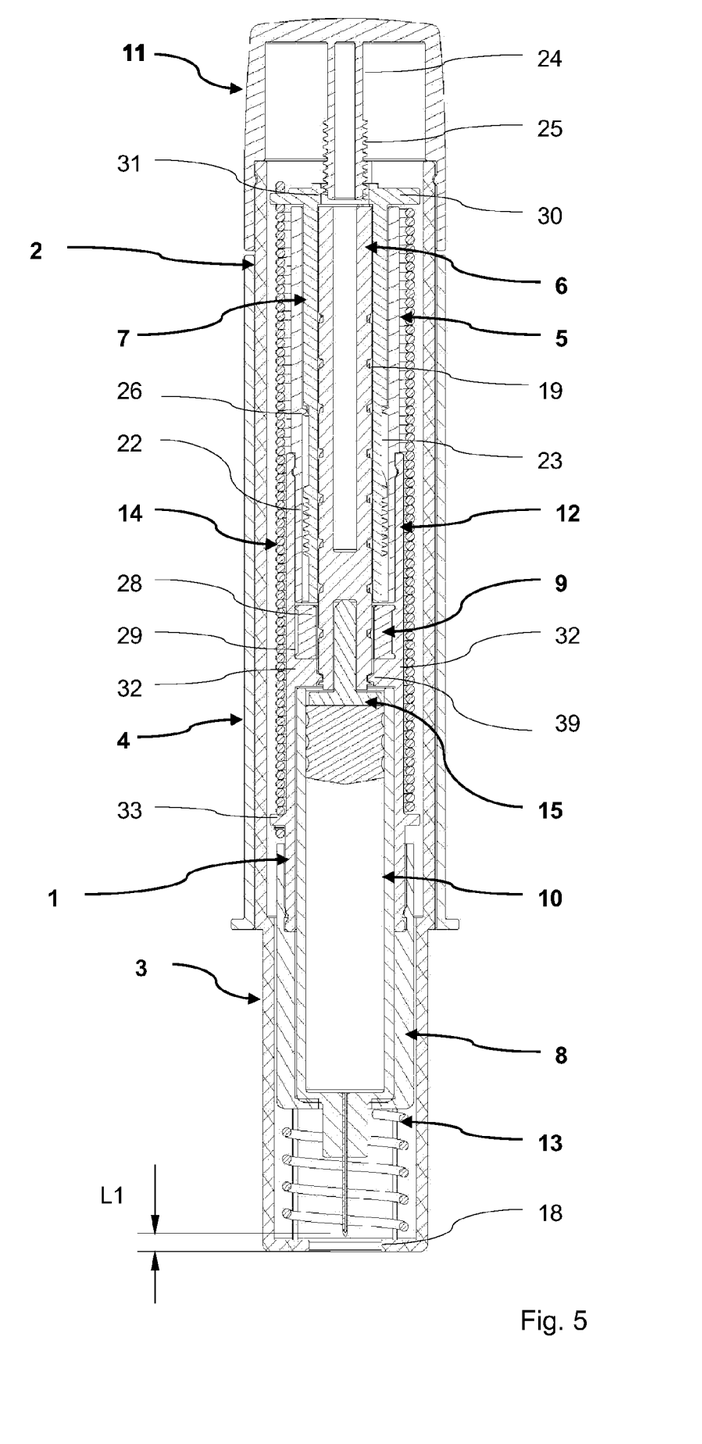
FIG. 5 schematically shows a vertical sectional view of an auto injector according to the invention, which is ready for use.

FIG. 5 shows a sectional view of an auto injector according to the invention. The cartridge 10 with the medicament, the hollow needle and the movable plunger is held within the interior of the syringe assembly 1, which further comprises the cartridge aligner 8 fixed to the cartridge carrier 12 and firmly enclosing the cartridge 10, the connecting tube 5 fixed to the cartridge carrier 12, the screw 6, the plunger foot 15 and the damper 9. The screw 6 with a thread 19 is extending through an orifice 32 in the cartridge carrier 12 and engaged with a thread 39 in a first thread engagement, and at the same time the screw 6 is abutting the plunger in the cartridge 10 via the plunger foot 15, which is rotational relative to the screw 6. The damper 9 is slowing down the rotational speed of the screw 6 before the needle is retracted to ensure that the full content is expelled. This will be further explained later.

A driver 7 is rotational but not axial connected with the screw 6 by means of keys 20 on the screw 6 (see FIG. 2) and grooves 43 inside the driver 7, and the two parts can telescope relative to each other. Arranged on the outside of the cartridge carrier 12 and the driver 7 is a pretensed torsion spring 14, which in one end 38 is fixed to a flange 33 on the cartridge carrier 12 and in the other end 38' is fixed to a flange 30 on the driver 7. From the top plate of the upper housing 11 a tube formed protrusion 24 with a thread 25 is protruding downward and engaged with a thread 31 inside the upper section of the driver 7 in a second thread engagement. The syringe assembly 1 is, via the connecting tube 5, connected in a first axial range with the driver 7 via a key 21 on the driver 7 and a slot 41 inside the connector tube 5 (see FIG. 2), in a second axial range, in which the parts rotates in a third thread engagement between the key 21 and a helical surface 27 with high pitch, and in a third axial range, in which the parts rotates in a fourth thread engagement between the thread 22 outside the driver 7 and the thread segment 26 inside the connector tube 5. During the rotation of the driver 7 in the third thread engagement 21/27 the thread segment 26 moves in the area between the helical segments 23 on the driver 7, but without contact to the helical segments. The pitch of the second and the fourth thread engagement are the same, and they are lower than the third thread engagement. In the lower end of the housing 2 an opening 18 is provided, through which the needle can be exposed and inserted when the auto injector is triggered. Between the syringe assembly 1 and the housing 2 a return spring 13 is arranged, the spring pushing the syringe assembly 1 back in the auto injector to hide the needle after the medicament has been injected, and biasing the syringe assembly 1 towards the tube formed protrusion 24 in top of the housing 2, so that the second thread engagement 25/31 between the tube formed protrusion 24 and the driver 7 is defining the axial position of the syringe assembly 1. After injection of the medicament the second thread engagement between disengages, and the return spring 13 pushes the syringe assembly 1 up in the auto injector so that the needle is hidden. This will be further explained later. The trigger sleeve 4, arranged on the outside of the housing 2, has two protrusions 36 protruding inwardly toward the main axis, both with a smaller section 37 even closer to the main axis (see FIG. 9). The two protrusions 36 protrude through openings 47 in the housing 2 (see FIG. 10), and mates with two protrusions 34 on the cartridge carrier 12, which are arranged on flexible arms 35 (see FIG. 8) to ease assembly of the auto injector, and which locks the syringe assembly 1 against rotation relative to the housing 2. When the trigger sleeve 4 is moved downward relative to the housing 2, the syringe assembly 1 is moved along, and the keys 21 (see FIG. 2) on the driver 7 are moved out of engagement with the slots 41 on the connector tube 5 (see FIG. 2), which causes the two parts to move from the first axial range into the second axial range, and the functional sequences of inserting the needle, injecting and retracting the needle begins.

In the following the functional sequences of triggering the auto injector, inserting the needle, expelling the medicament and retracting the needle will be explained in more details. In FIG. 5 an auto injector according to the invention is showed. The trigger sleeve 4 is in its upper position and is not yet activated by the user, and the keys 21 on the driver 7 is engaged with the slots 41 in the connecting tube 5 and thereby the trigger 7 is locked against rotation. The needle is hidden and retracted a distance L1 from the opening 18, and the cartridge 10 is full. The thread 31 on the driver 7 is pressed against the thread 25 on the tube formed protrusion 24 by the return spring 13, and these two threads 25/31 forming the second thread engagement have not yet fully engaged. It can also be seen that the thread segment 26 on the connecting tube 5 and the thread 22 on the driver 7 together forming the third thread engagement have also not yet been engaged.

Before the user can fire the auto injector, he must enable the device by rotating the trigger sleeve 4 a limited angle. The details of this operation will be further explained later.

Figure 6:
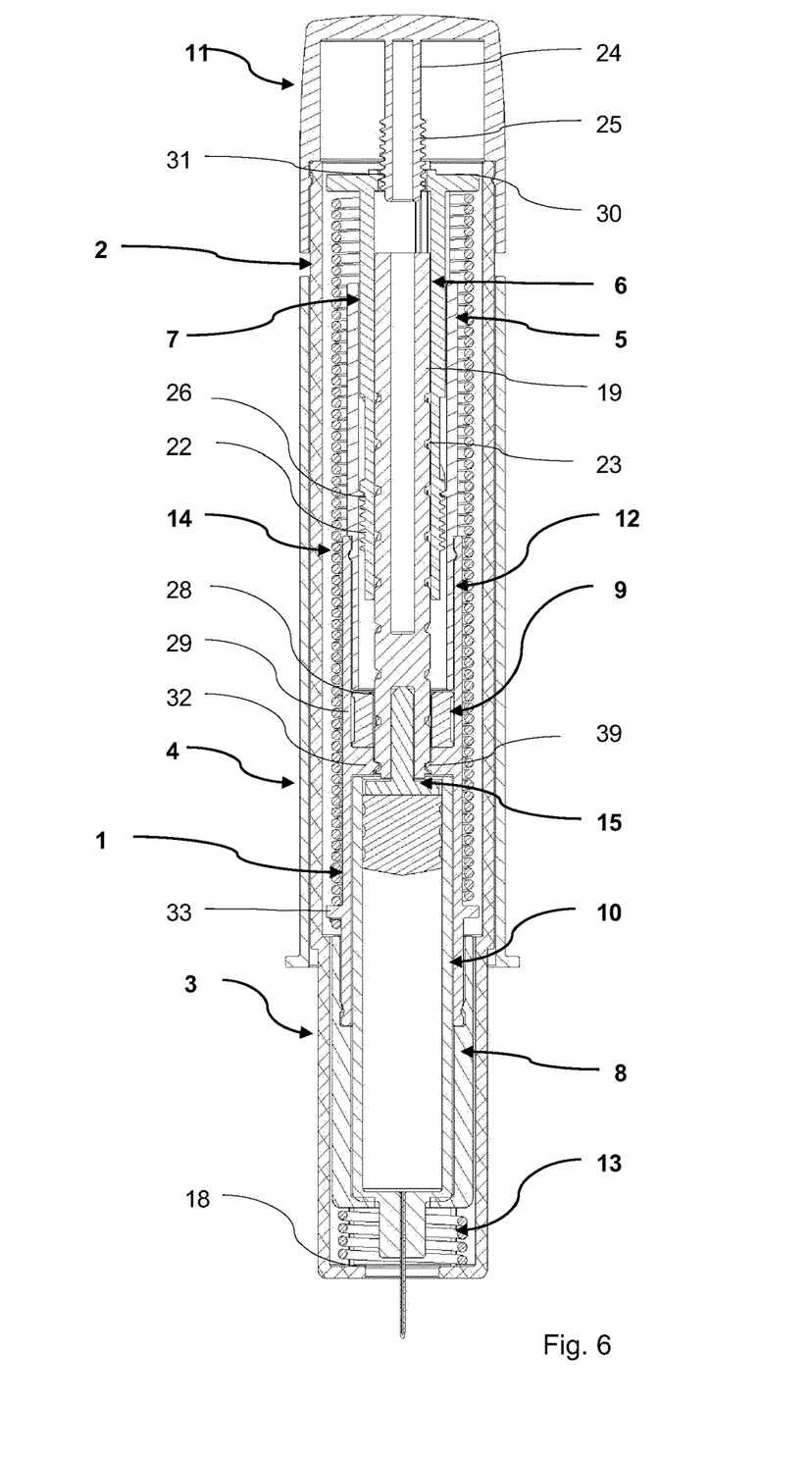
FIG. 6 schematically shows a vertical sectional view of an auto injector according to the invention, where the trigger is activated, and the needle is exposed.

In FIG. 6 the trigger sleeve 4 has been moved down toward the needle end and due to the axial contact between the protrusions 36 inside the trigger sleeve 4 and the protrusions 34 on the cartridge carrier 12 (see FIGS. 9 and 10) also the syringe assembly 1 has been moved downwards, and consequently the key/slot engagement 21/41 between the connecting tube 5 and the driver 7 has disengaged and moved from the first axial range to the second axial range, wherein the keys 21 and the helical surfaces 27 are engaged in the third thread engagement. Due to the pretensed torsion spring 14 this has in turn rotated the driver 7 and due to the high pitch moved the syringe assembly 1 rapidly forward so that the needle has been exposed and inserted at the injection site. Due to the second thread engagement 25/31 between the driver 7 and the upper housing 11 the driver 7 has also moved, but in the opposite direction of the syringe assembly 1, but because the pitch of the third thread engagement is much higher than the pitch of the second thread engagement, the result is still a rapid forward movement of the syringe assembly 1 and the needle. As the axial force acting on the connecting tube 5 due to the torsion spring 14 is much bigger than the counteracting force from the return spring 13, the return spring 13 is compressed.

Figures 9, 10, 11:
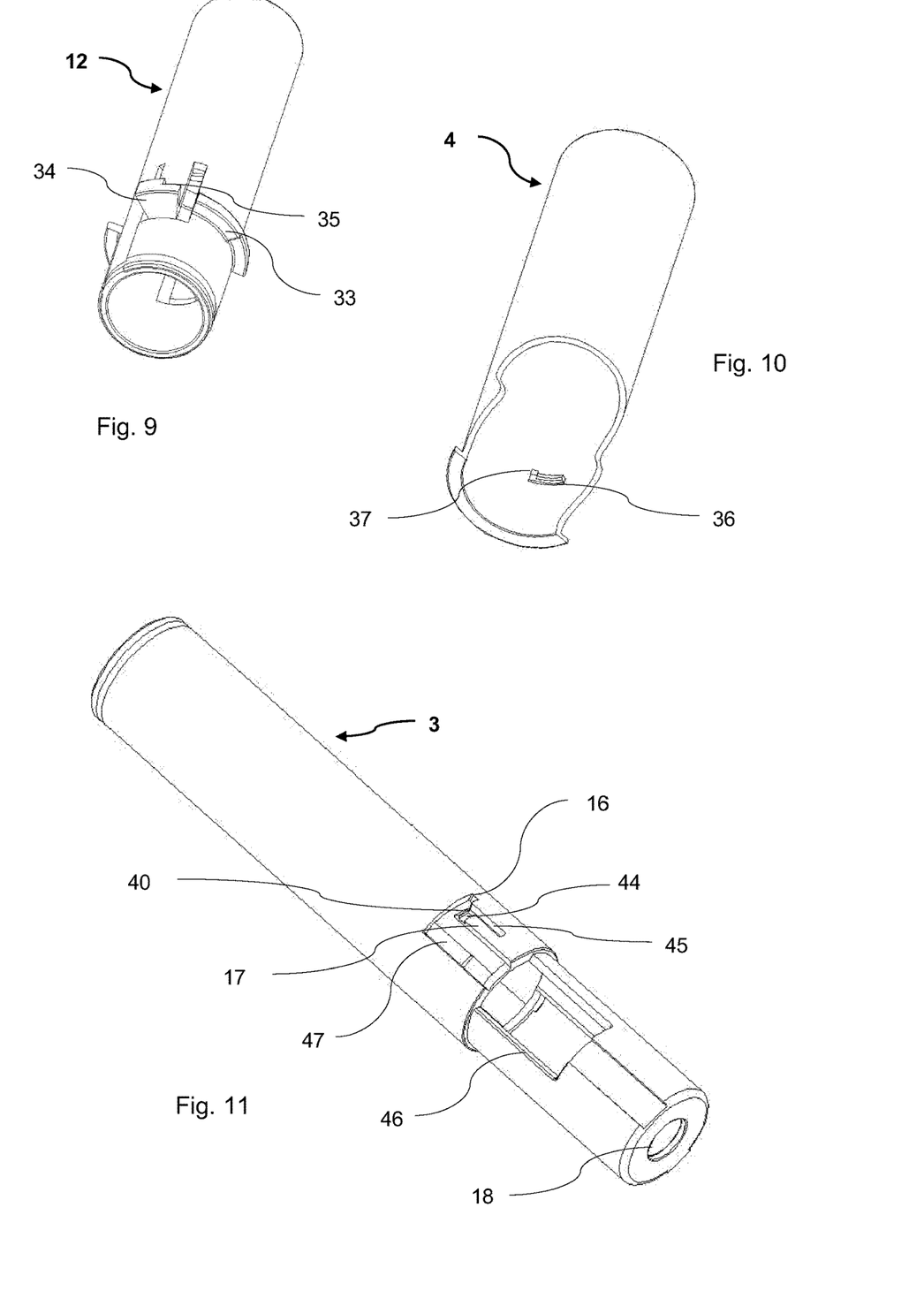
FIG. 9 shows a perspective view of the cartridge carrier according to the invention.
FIG. 10 shows a perspective view of the trigger sleeve according to the invention.
FIG. 11 shows a perspective view of the housing according to the invention.

The trigger sleeve 4 is only capable of moving a short distance to initiate the disengagement between the driver 7 and the connecting tube 5, and it is locked into this triggered position by the flexible arm 17 and the locking tooth 40 on the housing 3 (see FIG. 11).

After the forward movement of the syringe assembly 1, the driver 7 and the connecting tube 5 are ready to leave the second axial range and enter into the third axial range, and consequently the thread segment 26 on the connecting tube 5 is ready to engage the thread 22 on the driver 7 in the fourth thread engagement.

Figure 7:
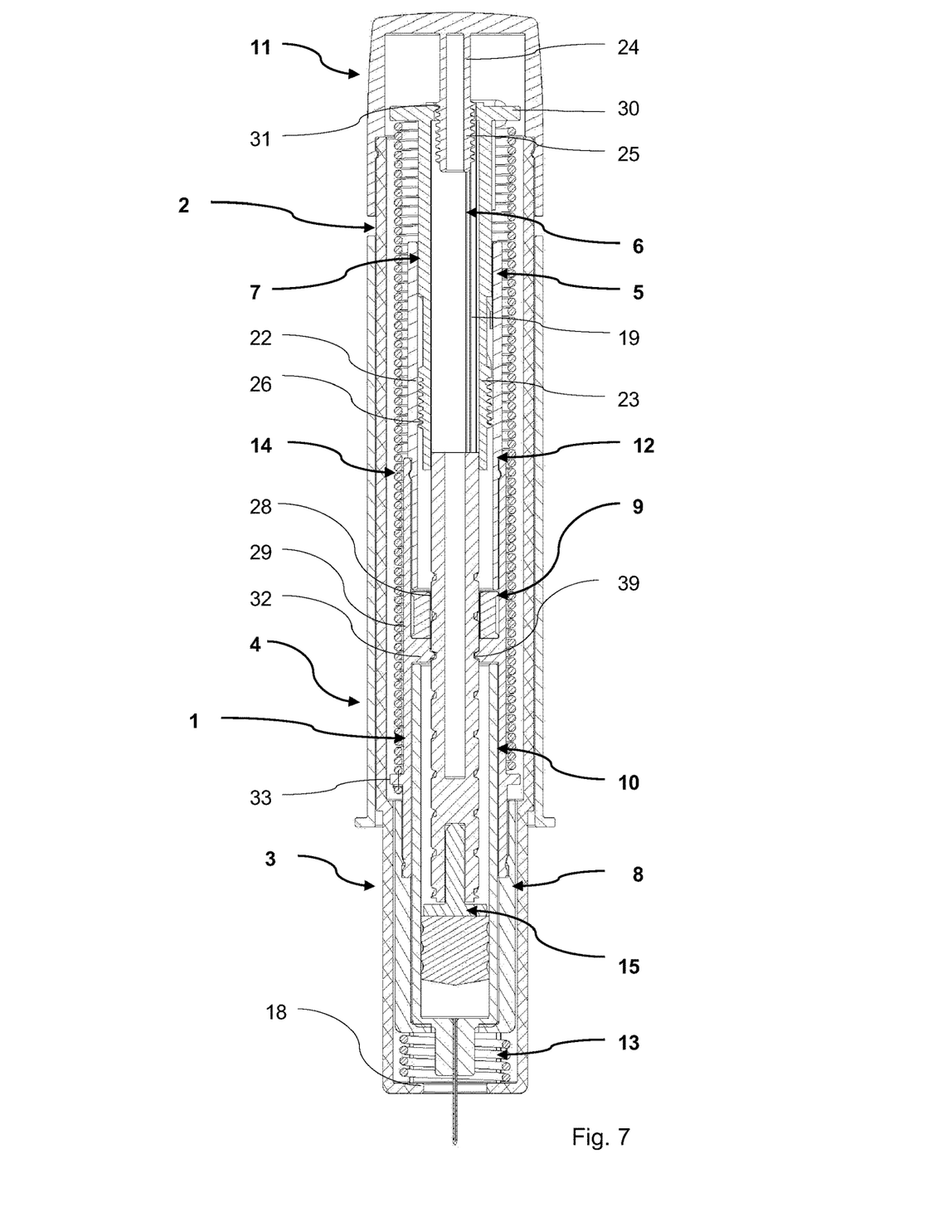
FIG. 7 schematically shows a vertical sectional view of an auto injector according to the invention, where the medicament has been injected.

In FIG. 7 almost the full content of the cartridge 10 have been expelled. It is clear that the plunger in the cartridge 10 has moved down pushed by the screw 6, due to the rotation of the screw 6 in the first thread engagement with the cartridge carrier 12 and driven by the rotation of the driver 7 and the torsion spring 14. The volume formed by the cartridge 10 and the plunger is hereby significantly reduced. As the second and the fourth thread engagements have the same pitch, the syringe assembly 1 has the same axial position. On FIG. 7 the driver 7 is still engaged with the thread 25 in the second thread engagement, and a rotation of approximately 90° remains before it disengages. The keys 20 on the screw 6 (see FIG. 2) are positioned just above the damper 9 and further downward movement of the screw 6 will cause the keys 20 to engage the teeth 28 inside the damper 9. Due to a damping high viscous compound 29 between the damper 9 and the cartridge carrier 12, the damper 9 can only be rotated slowly, and the speed of the screw 6 is slowed down, which in turn allows the plunger to fully relax and the full content of the cartridge to be expelled, before the needle is retracted. It is further advantageous if the thread 19 on the screw 6 is interrupted just after the keys 20 have engaged the teeth 28 on the damper, so that the screw 6 is not advanced down in the cartridge during the damping period.

Figure 8:
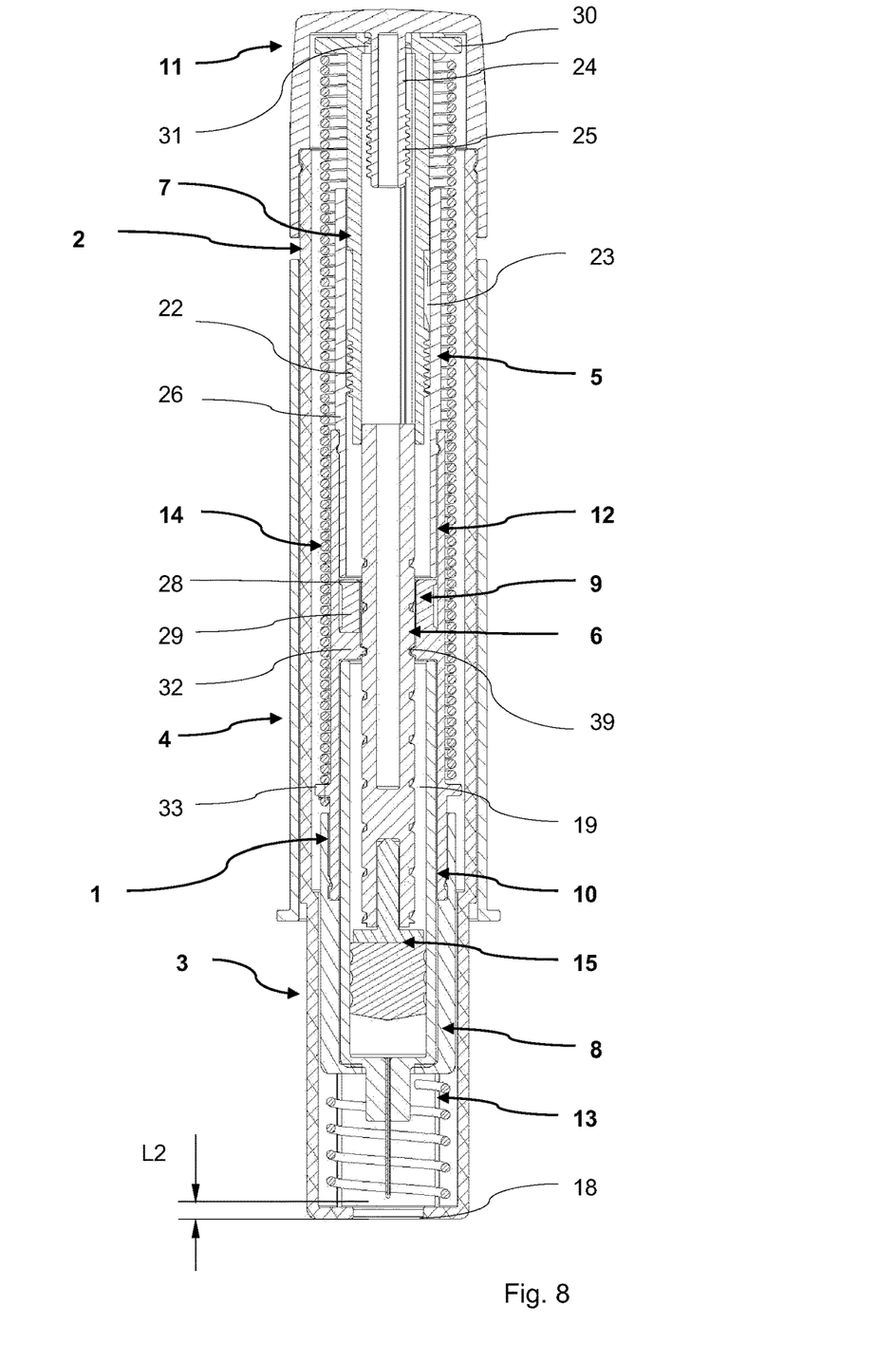
FIG. 8 schematically shows a vertical sectional view of an auto injector according to the invention, where the needle has been retracted from the exposed position.

FIG. 8 shows an auto injector according to the invention, where the syringe assembly with the needle is retracted back into the auto injector to an inaccessible position. The driver 7 has rotated the remaining angle in the second thread engagement, and the threads 25/31 of the driver 7 and the upper housing 11 have disengaged. This has caused the driver 7 and consequently the syringe assembly 1 to move up in the auto injector pushed by the return spring 13, until abutment between the protrusions 34 on the cartridge carrier 12 and the protrusions 36 inside the trigger sleeve 4. As there is no shifting mechanism or mode changing elements involved in the retraction of the syringe assembly 1, but simply threads 25/31 that ends and disengages, the retraction mechanism provides a big improvement compared to state-of-the-art auto injectors as no elements can lock and jam during the retraction sequence. As the trigger sleeve 4 is locked in the fired position, the syringe assembly 1 can only retract to the new position of the trigger sleeve 4 and the pre-injection distance L1 (see FIG. 5) is therefore a little longer than the post injection distance L2 (see FIG. 8).

Just after disengagement of the second thread engagement, the fourth thread engagement between the driver 7 and the connecting tube 5 reached a stop, and further rotation of the driver 7 relative to the connecting tube 5 was prevented. The gap between the trigger sleeve 4 and the upper housing 11, after the trigger sleeve 4 has been moved and locked in the triggered position, reveals the surface of the lower housing, and this surface may be used to indicate that the auto injector is now used and must be disposed e.g., by means of a symbol or a signal color on the surface.

In the following the functional details of unlocking the auto injector by enabling the axial movement of the trigger sleeve 4, and of locking the trigger sleeve 4 in the fired position after it has been triggered, will be explained. In the lower housing 3 two rectangular openings 47, in which the protrusions 34 on the cartridge carrier 12 (see FIG. 9) can move up and down, is provided, as can be seen on FIG. 11. During assembly the rectangular openings 47 allows the protrusions 36 inside the trigger sleeve 4 (see FIG. 10) to be moved from the needle end of the lower housing 3 to the upper end of the openings 47 and to be rotated into the locking position 16. After the syringe assembly 1 is mounted in the lower housing 3, the protrusions 36 inside the trigger sleeve 4 can no longer be fully moved into the openings 47 in the lower housing due to the vertical surface 35 on the protrusions 34 on the cartridge carrier 12, and these now acts as a rotational stop for the trigger sleeve 4. To enable the auto injector to be fired, the trigger sleeve 4 is rotated until the protrusion 36 abuts the surface 35 on the protrusions 34. Hereafter downward movements of the trigger sleeve 4 to fire the device causes the arms 17 with the teeth 40 on the lower housing 3 to bend inwardly towards the main axis and snap over the protrusions 36 to capture the teeth 40 in the slots 44, and the trigger sleeve 4 is thereby prevented from moving up or down. After the auto injector is fired the deeper areas 37 of the protrusions 36 are positioned in the slots 45, and the trigger sleeve 4 is hereby prevented from both rotational and axial movements.

The invention claimed is:

1. An auto injector defining a main axis and comprising:
    a housing including a needle end,
    a syringe assembly comprising a cartridge with a hollow needle, a plunger, and a medicament to be injected,
    a first spring,
    a driver,
    a screw, and
    a trigger adapted to initiate functional sequences of the auto injector after activation,
    wherein the functional sequences include moving the syringe assembly in one direction to expose the needle to an accessible position, expelling the medicament out through the needle, and moving the syringe assembly in the opposite direction to retract the needle to an inaccessible position,
    the screw 6 during injection is adapted to move the plunger in the cartridge to expel the medicament by means of the first spring and via the driver,
    the first spring is a torsional spring rotating the driver during expelling of the medicament, and
    the first spring in one end is fixed to the syringe assembly and in the other end to the driver.

2. The auto injector according to claim 1, wherein the screw and the driver are rotationally connected so that they rotate together but are allowed to telescope relatively, and so that the screw is rotated in a first thread engagement causing it to move toward the needle end.

3. The auto injector according to claim 1, wherein the screw and the driver are engaged in a first thread engagement and the movement of the plunger is the result of a rotational movement of the driver relative to the screw in the first thread engagement.

4. The auto injector according to claim 2, wherein the driver engages the housing in a second thread engagement at least during expelling of the medicament, and the second thread engagement at the end of the expelling of medicament disengages, so that the driver and the syringe assembly by means of a second spring is moved away from the needle end to a position where the needle is inaccessible.

5. The auto injector according to claim 1, wherein the syringe assembly and the driver during exposure of the needle are engaged in a third thread engagement and the axial movement of the syringe assembly during exposure of the needle is a result of relative rotational movement between the syringe assembly and the driver.

6. The auto injector according to claim 1, wherein the syringe assembly after initiation by means of the trigger is moved toward the needle end of the housing by means of a third spring being a compressible spring.

7. The auto injector according to claim 2, wherein the length and position of the thread on the screw is arranged such that rotation of the screw in the first thread engagement does not move the plunger in the cartridge during exposure and retraction of the needle.

8. The auto injector according to claim 1, wherein the functional sequences of the auto injector start after an axial movement of the driver relative to the syringe assembly and initiated by the trigger.

9. The auto injector according to claim 1, wherein the trigger is a sleeve movable arranged on the outside of the housing.

10. The auto injector according to claim 1, wherein the trigger must be rotated through an angle relative to the housing to enable initiation of the functional sequences of the auto injector, where-after axial movement of the trigger initiates the functional sequences.

11. The auto injector according to claim 1, wherein a damper rotatably arranged inside the syringe assembly rotationally connects to the screw at or near the end of expelling of medicament, to slow down the speed of the screw by means of friction.

* * * * *